US00PP21069P2

(12) United States Plant Patent
Korlipara

(10) Patent No.: US PP21,069 P2
(45) Date of Patent: Jun. 15, 2010

(54) ***COREOPSIS* PLANT NAMED 'PINK LADY'**

(50) Latin Name: ***Coreopsis* sp.**
Varietal Denomination: Pink Lady

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/321,459

(22) Filed: Jan. 20, 2009

(51) Int. Cl.
*A01H 5/00* (2006.01)

(52) U.S. Cl. ..... Plt./417

(58) Field of Classification Search ..... Plt./417
See application file for complete search history.

*Primary Examiner*—Kent L Bell
(74) *Attorney, Agent, or Firm*—Klarquist Sparkman, LLP

(57) ABSTRACT

A new and distinct *Coreopsis* plant named 'Pink Lady' characterized by medium sized, clear pink, daisy like flowers, very free flowering, a mounding habit, and excellent vigor.

1 Drawing Sheet

Botanical name: *Coreopsis* sp.
Variety designation: 'Pink Lady'.

BACKGROUND OF THE INVENTION

The present invention relates to a new and distinct plant of *Coreopsis* and given the cultivar name 'Pink Lady'. *Coreopsis* is in the family Asteraceae. This new cultivar originated as a seedling found in the nursery from unknown propriety plants in Canby, Oreg. and reproduced in tissue culture where further selections were made. This selection was made for its clear pink flowers.

SUMMARY OF THE INVENTION

The following traits have been repeatedly observed and are determined to be the unique characteristics of 'Pink Lady'. These characteristics in combination distinguish 'Pink Lady' as a new and distinct cultivar:

1. medium sized, clear pink, daisy like flowers,
2. mounding habit,
3. very free flowering
4. and excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one year old *Coreopsis* 'Pink Lady' growing in the ground in the field in August in Canby, Oreg.

DETAILED PLANT DESCRIPTION

The following is a detailed description of the new *Coreopsis* cultivar based on observations of a one-year-old specimen growing in the ground in the trial fields in August in Canby, Oreg. The color descriptions are all based on The Royal Horticultural Society Colour Chart.

Plant:
- *Type.*—Herbaceous perennial.
- *Hardiness.*—USDA Zones 9 to 10.
- *Size.*—40 cm wide and 30 cm tall to top of flowers.
- *Form.*—Mound with freely branching stems.
- *Vigor.*—Excellent.

Stem:
- *Type.*—Ascending.
- *Size.*—23 cm long and 2.5 mm wide.
- *Internode length.*—55 mm to 10 mm.
- *Surface.*—Glabrous.
- *Color.*—Yellow Green 148A.

Leaf:
- *Type.*—Simple.
- *Shape.*—Linear, occasionally with one narrow basal pinna.
- *Arrangement.*—Opposite.
- *Length.*—21 mm to 62 mm, sessile.
- *Width.*—1 mm to 5 mm.
- *Margins.*—Entire.
- *Apex.*—Acute.
- *Base.*—Attenuate.
- *Texture.*—Soft, smooth.
- *Surface texture.*—Glabrous on both sides.
- *Venation.*—Pinnate.
- *Color.*—Top and bottom side Green 137A.

Inflorescence:
- *Type.*—Composite, long stalked terminal heads of daisy type inflorescences.
- *Size.*—30 mm wide and 6 mm deep.
- *Peduncle.*—4 mm long and 0.5 mm wide, glabrous, Green 137A.
- *Immature.*—5 mm long and 5 mm wide, globular, glabrous, Greyed Purple 187B at the top and Green 146A on sides and base.
- *Ray florets.*—8 in number, sterile with no stamen or pistil, claw 3 mm long, each floret obovate with the tip three lobed and; lobes obtuse and the central lobe the longest, base attenuate, grows to 15 mm long, 9 mm wide, entire, glabrous on both sides, topside color between Red Purple 70C and Red Purple 69A, bottom side the same but lighter.

*Disc.*—Overall conic in shape when mature, cone grows to 6.5 mm wide and becoming 4 mm deep with maturity, colored Greyed Red 178A when young, opening to orange, Orange 25A with a dark background, Black 102A.

*Disc florets.*—About 50 in number, each floret 3 mm long and 0.5 mm wide, tubular with 4 lobes, lobes Greyed Orange 177A, tube Greyed Orange 165C; pistil one in number, 3 mm long, extruding, 2-branched stigma, Greyed Orange 177A; stamen 5 in number, Black 202A; pollen Orange 24A.

*Phyllaries.*—In two series; inside series is larger at 12 mm wide with 8 lobes, each 6 mm long and 3 mm wide, shape obovate, margin entire, tip acute, Orange 25A; on top and bottom; outside series is 5 mm wide with 6 to 8 lobes, each 1.5 mm long and 1 mm wide, top and bottom side Green 137A.

*Receptacle.*—2 mm wide and 1.5 mm deep, bowl shaped, Green 137A.

*Bloom period.*—May through August in Canby, Oreg.

*Fragrance.*—Light, daisy like.

*Lastingness.*—Each inflorescence lasts about a week.

Fruit:

*Type.*—Achene, not fully formed.

*Fertility.*—Infertile.

Seed: None produced.

Disease and pests: *Coreopsis* are susceptible to mildew and fungal spots. None of these have been observed on plants grown under commercial conditions in Canby, Oreg.

COMPARISONS TO SIMILAR *COREOPSIS*

Compared to *Coreopsis* 'Limerock Ruby' (U.S. Plant Pat. No. 15,455), this new cultivar has light pink flowers rather than ruby red and a more mounding habit.

I claim::

1. A new and distinct *Coreopsis* plant herein illustrated and described.

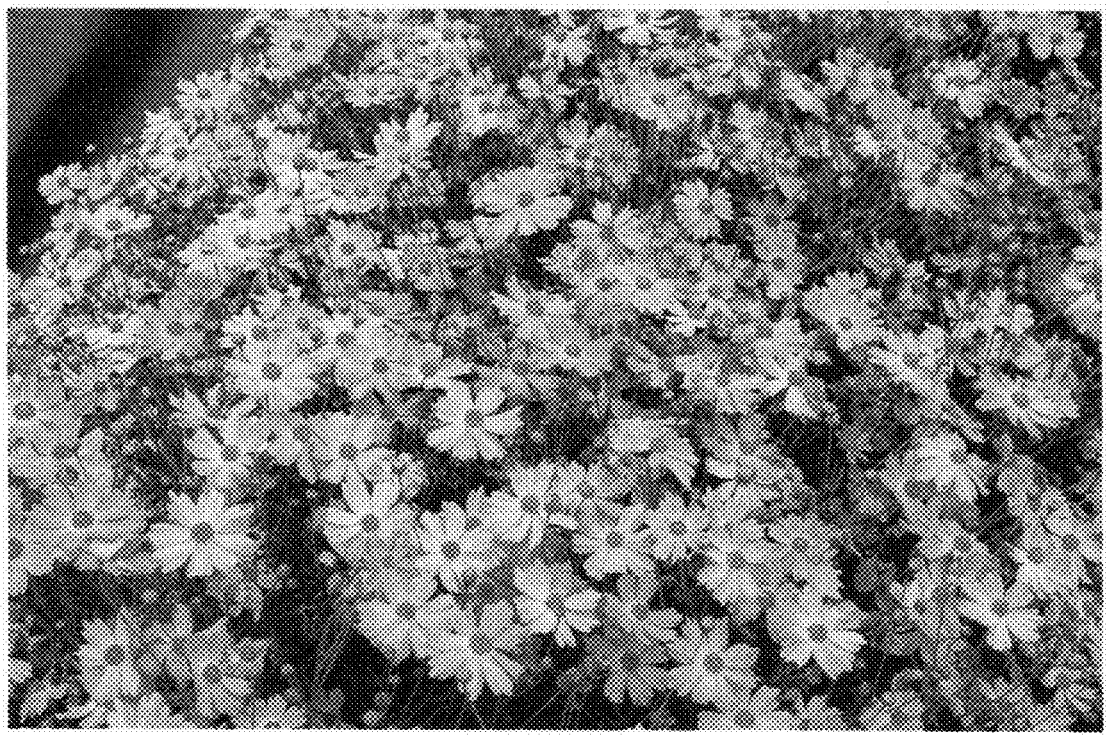

* * * * *